US011547478B2

(12) United States Patent
Hancock et al.

(10) Patent No.: US 11,547,478 B2
(45) Date of Patent: Jan. 10, 2023

(54) ELECTROSURGICAL APPARATUS AND METHOD OF TISSUE ABLATION

(71) Applicant: CREO MEDICAL LIMITED, Monmouthshire (GB)

(72) Inventors: Christopher Paul Hancock, Bath (GB); Patrick Burn, Chepstow (GB); Charlie Campion, Bristol (GB); Louis Turner, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 825 days.

(21) Appl. No.: 16/481,411

(22) PCT Filed: May 3, 2018

(86) PCT No.: PCT/EP2018/061316
§ 371 (c)(1),
(2) Date: Jul. 26, 2019

(87) PCT Pub. No.: WO2018/202758
PCT Pub. Date: Nov. 8, 2018

(65) Prior Publication Data
US 2019/0380778 A1    Dec. 19, 2019

(30) Foreign Application Priority Data

May 4, 2017   (GB) .................................... 1707112

(51) Int. Cl.
*A61B 18/00*   (2006.01)
*A61B 18/18*   (2006.01)
(Continued)

(52) U.S. Cl.
CPC ..... *A61B 18/1815* (2013.01); *A61M 25/0084* (2013.01); *A61B 17/3478* (2013.01);
(Continued)

(58) Field of Classification Search
CPC ............ A61B 17/3478; A61B 18/1815; A61B 2017/0034; A61B 2018/00196;
(Continued)

(56) References Cited

U.S. PATENT DOCUMENTS

2011/0004205 A1    1/2011  Chu et al.
2016/0022349 A1*   1/2016  Woloszko .............. A61B 18/14
                                                              606/34
(Continued)

FOREIGN PATENT DOCUMENTS

JP           4-22350 A       1/1992

OTHER PUBLICATIONS

International Search Report and Written Opinion, issued by International Searching Authority in corresponding International Application No. PCT/EP2018/061316, dated Aug. 17, 2018, (PCT/ISA/210, PCT/ISA/220 & PCT/ISA/237).

(Continued)

*Primary Examiner* — George Manuel
(74) *Attorney, Agent, or Firm* — ArentFox Schiff LLP

(57) ABSTRACT

An electrosurgical apparatus for treating fluid-filled biological growths by replacing the fluid within the growth with a substance that assists in delivering treatment energy. The treatment energy may be microwave energy or may be thermal energy derived from microwave energy. The apparatus comprises an instrument having a radiating tip portion, and a fluid delivery mechanism for transporting fluid to and from a treatment zone located around the radiating tip portion. The fluid delivery mechanism comprises a rigid insertion element arranged to extend into the treatment zone, whereby fluid can be aspirated from the treatment zone, and a substance injected into the treatment zone to replace the aspirated fluid. The injected substance has dielectric prop- (Continued)

erties selected to facilitate uniform delivery of treatment energy to biological tissue in the treatment zone.

16 Claims, 5 Drawing Sheets

(51) Int. Cl.
  *A61M 25/00* (2006.01)
  *A61B 17/34* (2006.01)
  *A61B 17/00* (2006.01)
(52) U.S. Cl.
  CPC ............... *A61B 2017/0034* (2013.01); *A61B 2018/00494* (2013.01); *A61B 2018/00577* (2013.01); *A61B 2018/00982* (2013.01); *A61B 2018/1861* (2013.01); *A61B 2218/002* (2013.01); *A61B 2218/007* (2013.01); *A61M 2025/0089* (2013.01)
(58) Field of Classification Search
  CPC ........... A61B 2018/00494; A61B 2018/00577; A61B 2018/00982; A61B 2018/1861; A61B 2018/1869; A61B 2018/1884; A61B 2018/1892; A61B 2218/002; A61B 2218/007; A61M 2025/0089; A61M 25/0084
  See application file for complete search history.

(56) References Cited

U.S. PATENT DOCUMENTS

2016/0051327 A1  2/2016  Brannan
2016/0317218 A1  11/2016 Sigmon, Jr. et al.
2017/0118806 A1  4/2017  Chu et al.

OTHER PUBLICATIONS

Search Report under Section 17(5), issued in counterpart British Patent Application No. GB1707112.7, dated Oct. 9, 2017.
Communication from the Japanese Patent Office in counterpart application No. 2019-543939, dated Mar. 15, 2022.

\* cited by examiner

ELECTROSURGICAL APPARATUS AND METHOD OF TISSUE ABLATION

CROSS-REFERENCE TO RELATED APPLICATIONS

This application is a National Stage entry of International Application No.: PCT/EP2018/061316, filed May 3, 2018, which claims priority to Great Britain Patent Application No. 1707112.7, filed May 4, 2017. The disclosures of the priority applications are hereby incorporated in their entirety by reference.

FIELD OF THE INVENTION

The invention relates to an electrosurgical apparatus and method for ablating biological tissue using microwave energy. In particular, the invention relates to the ablation of biological growths, such as cysts or tumours, especially where such growths contain fluid. The invention may find particularly use in treating pancreatic cysts or tumours.

BACKGROUND TO THE INVENTION

It is inherently difficult to gain access to growths such as tumours or cysts in the pancreas due to the location of the pancreas and its proximity to other organs. Additionally, the margins between a growth's boundary and the pancreatic wall are often very small. Because of this, there is a high risk of collateral damage to other organs during surgical procedures to treat or remove pancreatic tumours or cysts. As a result, many treatment options are employed, such as chemotherapy, radiotherapy, and different types of surgery. Surgical procedures can involve partial or total pancreatectomy (removal of the pancreas), stent placement or bypass surgery (e.g. to relieve a blocked bile duct) or enucleation (removal of just the tumour/cyst). Depending on the type of surgery, the pancreas may be accessed by open surgery (e.g. using a large incision in the abdomen), or via a keyhole incision using a laparoscope.

The morphology of cysts and tumours within the pancreas is varied and can consist of a solid mass, one or more open voids, or a mixture of solid mass and open voids. The open voids (or sacs) are filled with cystic fluids such as serous fluid or mucinous fluid. The fluid-filled sacs within a single tissue growth may be in communication with each other (i.e. there are passages connecting them), or may be separate (i.e. without any connection between them).

A known method for detecting and imaging pancreatic cysts and tumours is endoscopic ultrasound (EUS). In this method, an endoscope is inserted into the patient's mouth and advanced through the oesophagus and stomach until it is in the vicinity of the duodenum. An ultrasound probe on the endoscope is used to obtain high quality images of the surrounding organs. Because of the proximity of the pancreas to the duodenum, very detailed ultrasound images of the pancreas can be obtained. Additionally, a pancreatic biopsy can be obtained during an EUS procedure, using a fine hollow needle on the endoscope. The needle is used to pierce the duodenal or stomach wall at an appropriate location so that it can be inserted into the pancreas. The ultrasound images can be used to accurately guide the needle to a desired location in the pancreas, such as a specific mass or cyst. Fluid from the pancreas or growth is then aspirated through the needle and collected so that it may be examined. This procedure is known as fine-needle aspiration (FNA).

SUMMARY OF THE INVENTION

At its most general, the present invention provides an electrosurgical technique for effectively treating fluid-filled biological growths by replacing the fluid within the growth with a substance that assists in delivering treatment energy. The treatment energy may be microwave energy or may be thermal energy derived from microwave energy, e.g. by dielectric heating.

By appropriately selecting the substance which is to be injected into the growth void, transmission of microwave and/or thermal energy to the growth tissue can be optimised, thus providing more efficient growth ablation. Conventional microwave ablation instruments usually have a symmetrical radiation profile, making the ablation of irregular or non-symmetrical growths difficult. By filling the void with a substance for transmitting energy to growth tissue, irregular or non-symmetrical growths can be ablated more effectively. The electrosurgical device can be configured to be fed through the working channel of an endoscope, so that it can be used to carry out minimally invasive surgical procedures.

According to a first aspect of the invention, there is provided an electrosurgical apparatus for treating a biological growth that contains a fluid-filled sac, the apparatus comprising: an electrosurgical instrument for delivering microwave energy into biological tissue, the electrosurgical instrument comprising: a coaxial cable for conveying microwave energy; and a radiating tip portion disposed at a distal end of the coaxial cable to receive microwave energy from the coaxial cable; and a fluid delivery mechanism for transporting fluid to and from a treatment zone located around the radiating tip portion, wherein the fluid delivery mechanism comprises: a flexible fluid conveying conduit that extends along the coaxial cable, and a rigid insertion element in fluid communication with a distal end of the fluid conveying conduit and arranged to extend into the treatment zone, wherein the fluid delivery mechanism is arranged: to aspirate fluid from the treatment zone, and to inject a substance into the treatment zone to replace the aspirated fluid, and wherein the substance has dielectric properties selected to facilitate uniform delivery of treatment energy to biological tissue in the treatment zone.

In use, the treatment zone may include a fluid-filled sac contained within a biological growth. The fluid delivery mechanism may be arranged to replace biological fluid in the fluid-filled sac with the substance before microwave energy is applied to treat. The treatment energy may be targeted at the biological tissue that surrounds (i.e. provides an inner wall of) the fluid-filled sac. Use of the substance may enable that biological tissue to receive uniform treatment.

The radiating tip portion may comprise a microwave antenna. The antenna may be a conventional monopole antenna formed on the end of the coaxial feed cable. An inner conductor of the coaxial feed cable may be connected to a radiating tip of the microwave antenna from which microwave energy can radiate. The radiating tip may include one or more dielectric materials to provide dielectric loading of the antenna, in order to enhance or shape the energy emission profile of the microwave antenna. In certain embodiments, the electrosurgical instrument may include multiple monopole antennae connected to the coaxial feed cable, in order to emit energy over a broader area. The multiple monopole antennae may be connected to the coaxial cable by a suitable power splitter arrangement. The antennae may be radially extendable to occupy a larger volume in the treatment zone.

The electrosurgical instrument can be used to apply microwave energy to matter in its vicinity, such as biological tissue, fluids or other materials. Microwave energy can cause dielectric heating in biological tissue, which can be used to ablate tissue in a localised volume around the antenna. Therefore, by inserting the antenna directly into a growth such as a cyst or a tumour, microwave energy can be applied to the growth tissue in order to ablate it.

Herein, the terms "proximal" and "distal" refer to the ends of the energy conveying structure further from and closer to the treatment site respectively. Thus, in use the proximal end is closer to a generator for providing the microwave energy, whereas the distal end is closer to the treatment site, i.e. the patient.

The term "conductive" is used herein to mean electrically conductive, unless the context dictates otherwise.

The term "longitudinal" used below refers to the direction along the instrument channel parallel to the axis of the coaxial transmission line. The term "lateral" refers to a direction that is perpendicular to the longitudinal direction. The term "inner" means radially closer to the centre (e.g. axis) of the instrument channel. The term "outer" means radially further from the centre (axis) of the instrument channel.

The term "electrosurgical" is used in relation an instrument, apparatus or tool which is used during surgery and which utilises microwave electromagnetic (EM) energy. Herein, "microwave EM energy" may mean electromagnetic energy having a stable fixed frequency in the range 300 MHz to 100 GHz, preferably in the range 1 GHz to 60 GHz. Preferred spot frequencies for the microwave EM energy include 915 MHz, 2.45 GHz, 5.8 GHz, 14.5 GHz, 24 GHz. 5.8 GHz may be preferred.

The fluid delivery mechanism enables fluid to be aspirated from a void in a growth, for example cystic fluid from a void in a cyst. Following aspiration of the fluid, the fluid delivery mechanism is configured to inject a substance into the void. The fluid delivery system may be configured to detect that a volume of fluid has been aspirated, and in response to detecting a particular volume, it is configured to inject the substance. In certain embodiments, the fluid delivery mechanism is configured to inject a volume of the substance into the void in the growth equal to a volume of the fluid aspirated from the void in the growth. This ensures that the amount of substance injected into the void in the growth will completely fill the void and maximises the contact area between the substance and the growth tissue. The substance can then transmit energy to all parts of the internal walls of the void. Controlling the amount of substance injected in this manner also ensures that the void is not overfilled, which could cause the growth to rupture and substance to flow out from the void.

The rigid insertion element may comprise a hollow needle. The hollow needle may be positioned at a distal end of the fluid delivery mechanism. The hollow needle may have a sharp end so that it can be used to pierce the wall of an organ and be inserted at a desired location into the organ. For example, the needle may be used to pierce through the duodenal wall so that the needle may be inserted into the pancreas. Fluid can be aspirated through the hollow needle so that it passes through the fluid conduit.

The fluid delivery mechanism may be separate from the electrosurgical instrument, or it may be integrated with the electrosurgical instrument. In embodiments where they are separate, the electrosurgical instrument and fluid delivery mechanism may be configured to be inserted separately into the working channel of an endoscope. For example, the fluid delivery mechanism can first be inserted into the working channel of an endoscope to aspirate fluid from a void in a growth and, if appropriate, inject a substance into the growth. The fluid delivery mechanism can then be removed from the working channel and the electrosurgical instrument inserted into the working channel. The antenna of the electrosurgical instrument can then be inserted into the aspirated void of the growth so that ablation of the growth tissue may be carried out.

In embodiments where the fluid delivery mechanism is integrated with the electrosurgical instrument, the fluid delivery mechanism and electrosurgical instrument can be fed simultaneously into the working channel of an endoscope. In certain embodiments, the rigid insertion element is mounted near the distal end of the electrosurgical instrument. For example the rigid insertion element may be secured to the radiating tip portion. The fluid conduit and coaxial feed cable may be housed in a single protective sheath running along part or all of their lengths. The integration of the two components provides a compact device and simplifies ablation procedures, as it does not require different components to be inserted into or removed from the working channel of an endoscope during an ablation procedure.

In another example, the coaxial cable may comprise an inner conductor, an outer conductor, and a first dielectric material separating the inner conductor and outer conductor. The inner conductor may be hollow to provide a passageway for the fluid delivery mechanism. The rigid insertion element may be in fluid communication with the flexible fluid conveying conduit via the passageway. The rigid insertion element (e.g. hollow needle) may be slidably mounted in the passageway.

The rigid insertion element may be movable between an exposed position where it protrudes beyond the distal end of the electrosurgical instrument, and a retracted position in which it is set back from the distal end of the electrosurgical instrument. The rigid insertion element may be moved between the two positions using one or more control wires. This enables the rigid insertion element to be deployed only when the user wishes to make use of the fluid delivery system, so that the rigid insertion element does not cause any accidental injuries when the fluid delivery system is not in use.

The distal end of the electrosurgical instrument may also include a sheath or protective hull which covers the rigid insertion element when it is in the retracted position, to further improve safety.

The fluid delivery mechanism may include two separate containers at a proximal end thereof. A first container may be for receiving the aspirated fluid. A second container may be for holding the substance to be injected. While the fluid is aspirated, the first container can be connected to the fluid conduit at the proximal end of the fluid delivery mechanism, so that aspirated fluid can be collected in the first container. Optionally, the first container can include a mechanism for detecting an amount of fluid collected (e.g. by measuring its weight and/or volume). The fluid is aspirated through the needle and the fluid conduit by creating a suction force in the fluid conduit, for example by using a syringe or a pump. To inject the substance, the first container is disconnected from the fluid conduit and the second container is connected to the fluid conduit. The substance may be caused to flow down the fluid conduit and rigid insertion element using a piston attached to the second container. The connection and disconnection of the containers can be carried out manually by the user, or can be carried out automatically by a controller, for example using a controllable valve system.

The electrosurgical instrument may be configured to, following the injection of the substance into the void in the growth, deliver microwave energy to the substance. This causes microwave energy and/or thermal energy to be transmitted via the substance to the growth tissue. This allows energy to be transferred from the antenna to the growth tissue more efficiently. Additionally, it enables irregular or non-symmetrical growths to be ablated more effectively, as the substance in the void causes the energy emitted by the antenna to be distributed more evenly around the walls of the void. The substance which is injected into the void can enhance the transmission of energy to growth tissue in several ways.

In one example, the substance may serve to transmit thermal energy from heated portions of tissue or substance to cooler portions of tissue or substance. The transmission of thermal energy to the growth tissue is achieved by using a substance which has a high dielectric loss factor at the microwave energy frequency used. In other words, the substance may consist of or comprise a dielectric fluid, such as de-ionised water or saline. When microwave energy is applied to the substance, the substance heats up and imparts thermal energy to the surrounding growth tissue, thus causing ablation of the growth tissue.

In contrast, the substance may provide dielectric loading for the antenna, in order to improve the efficiency of microwave energy delivery to the growth tissue. For example, if a substance is used which has a low dielectric loss factor at the microwave energy frequency, the substance will act as a conduit for efficiently transmitting microwave energy to the growth tissue. The dielectric loss factor is related to the imaginary part of a material's permittivity, and is indicative of energy dissipation in the material.

The substance may also be selected to effectively extend the radiating tip portion in order to produce a non-symmetrical radiation profile in order to match the shape of the void.

The substance may include a variety of fluids, gels or other suitable materials. In certain embodiments, the substance may be selected to transition from a liquid phase to a solid phase during application of microwave energy to the treatment zone. The hardening of the substance may be caused by a small rise in temperature arising from the application of microwave energy. Preferably the substance has a low dielectric loss factor at the microwave energy frequency, so that the hardened substance may act as an efficient means for transmitting the microwave energy from the microwave antenna into the wall of the void. This enables the microwave energy to be distributed around the walls of the void, even in cases where the void is irregular or non-symmetrical in shape, so that the growth may be effectively ablated.

The electrosurgical instrument may comprise an ultrasound probe for producing images of a patient's internal organs. The images produced by the ultrasound probe may be used to guide the growth ablation device to a desired location inside the patient. For example the ultrasound images may be used to guide the hollow needle to a cyst in the pancreas. The ultrasound probe may for example be mounted near the distal end of the electrosurgical instrument.

The electrosurgical apparatus discussed above may form part of an complete electrosurgical system. The system may further comprise a generator for generating the microwave energy, and a surgical scoping device for non-percutaneous insertion into a patient's digestive tract. The surgical scoping device may have an instrument channel running along its length, wherein the electrosurgical instrument and fluid delivery mechanism are conveyed within the instrument channel of the surgical scoping device. The coaxial cable is connected to receive the microwave energy from the generator.

Also disclosed herein is a method for treating a biological growth that contains a fluid-filled sac, the method comprises: non-percutaneously inserting an instrument cord of a surgical scoping device into a patient's digestive tract, the surgical scoping device having an instrument channel running along its length; conveying an electrosurgical instrument and a fluid delivery mechanism along the instrument channel of the surgical scoping device, wherein the electrosurgical instrument comprises a coaxial cable for conveying microwave energy, and a radiating tip portion disposed at a distal end of the coaxial cable to receive microwave energy from the coaxial cable, and wherein the fluid delivery mechanism comprises a flexible fluid conveying conduit that extends along the coaxial cable, and a rigid insertion element in fluid communication with a distal end of the fluid conveying conduit; extending the rigid insertion element into a fluid-filled sac contained within a biological growth located at the distal end of the instrument cord; aspirating fluid from the fluid-filled sac; injecting a substance into the fluid-filled sac to replace the aspirated fluid; and delivering microwave energy to the radiating tip portion, wherein the substance has dielectric properties selected to facilitate uniform delivery of treatment energy to biological tissue surrounding the fluid-filled sac. Any feature of the electrosurgical apparatus and system discussed herein my be utilised in the method.

BRIEF DESCRIPTION OF THE DRAWINGS

Examples of the invention are discussed below with reference to the accompanying drawings, in which.

DETAILED DESCRIPTION

Figure 1:
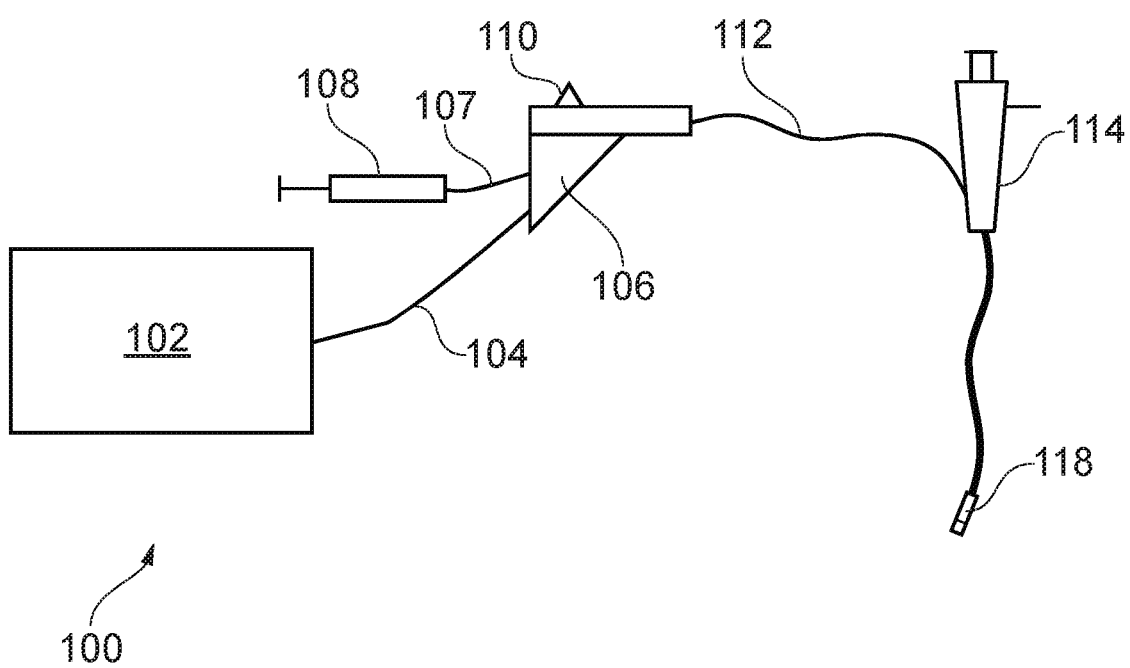
FIG. 1 is a schematic diagram of an electrosurgical apparatus for tissue ablation that is an embodiment of the invention.

FIG. 1 is a schematic diagram of a complete electrosurgical apparatus 100 that is an embodiment of the invention. The apparatus 100 is arranged to treat a fluid-filled biological growth (e.g. a cyst or tumour, referred to herein simply as a "growth", which contains one or more sacs of fluid). The apparatus 100 is capable of removing fluid from a void in a biological growth, injecting a substance into the void in the growth, and ablating the growth by applying microwave energy. As discussed below, the injected substance facilitates the delivery of energy to the cyst. The delivered microwave energy may be used to ablate biological tissue at an inside wall of the cyst, e.g. to remove and/or prevent regrowth of unwanted tissue, or to stop or prevent more fluid from filling the voids. In some embodiments, after treatment, the substance may be removed from the void.

The system 100 comprises a generator 102 for controllably supplying microwave energy. A suitable generator for this purpose is described in WO 2012/076844, which is incorporated herein by reference. The generator may be arranged to monitor reflected signals received back from the instrument in order to determine an appropriate power level for delivery. For example, the generator may be arranged to calculate an impedance seen at the distal end of the instrument in order to determine an optimal delivery power level.

The generator 102 is connected to an interface joint 106 by an interface cable 104. The interface joint 106 is also connected to a fluid delivery device 108, such as a syringe, via a fluid conduit 107. If needed, the interface joint 106 can house an instrument control mechanism that is operable by sliding a trigger 110, e.g. to control longitudinal (i.e. back and forth) movement of one or more control wires or push rods (not shown). If there is a plurality of control wires, there may be multiple sliding triggers on the interface joint to provide full control. The function of the interface joint 106 is to combine the inputs from the generator 102, fluid delivery device 108 and instrument control mechanism into a single flexible shaft 112, which extends from the distal end of the interface joint 106.

The flexible shaft 112 is insertable through the entire length of a working (instrument) channel of a surgical scoping device 114, such as an endoscope, gastroscope, laparoscope or the like. The flexible shaft 112 has a distal assembly 118 (not drawn to scale in FIG. 1) that is shaped to pass through the working channel of the surgical scoping device 114 and protrude (e.g. inside the patient) at the distal end of the surgical scoping device's working channel. The distal end assembly 118 includes a microwave antenna for delivering microwave energy and a hollow needle (not shown) fluidly connected to the fluid conduit 107 for aspirating and injecting fluids. The tip configuration is discussed in more detail below. The fluid delivery device 108, fluid conduit 107 and hollow needle form a fluid delivery system which enables fluid to be aspirated from, and a substance to be injected into, a target area. Different fluid delivery devices 108 can be connected to the fluid conduit 107, depending on the fluid to be aspirated or the substance to be injected.

The structure of the distal assembly 118 may be arranged to have a maximum outer diameter suitable for passing through the working channel. Typically, the diameter of a working channel in a surgical scoping device such as an endoscope is less than 4.0 mm, e.g. any one of 2.8 mm, 3.2 mm, 3.7 mm, 3.8 mm. The length of the flexible shaft 112 can be equal to or greater than 1.2 m, e.g. 2 m or more. In other examples, the distal assembly 118 may be mounted at the distal end of the flexible shaft 112 after the shaft has been inserted through the working channel (and before the instrument cord is introduced into the patient). Alternatively, the flexible shaft 112 can be inserted into the working channel from the distal end before making its proximal connections. In these arrangements, the distal end assembly 118 can be permitted to have dimensions greater than the working channel of the surgical scoping device 114.

The apparatus described above is one way of introducing the device. Other techniques are possible. For example, the device may also be inserted using a catheter.

The invention seeks to provide a device that can ablate a growth by applying microwave energy directly to the growth tissue and/or via a substance which is injected into the growth. The device is particularly suited to the ablation of growths in the pancreas, such as cysts or tumours, however it may also be used to ablate growths in other organs. In order to ablate a growth, the microwave antenna and hollow needle should be located as close as possible to (and in many cases inside) the target growth. In order to reach the pancreas, the device will therefore need to be guided through the digestive tract and around various obstacles. This means that the device will ideally be flexible and have a small cross section. Particularly, the device should be very flexible near its tip, where it may need to be steered to cut through the duodenal wall to gain access to the pancreas. The distal assembly 118 may also include an ultrasound probe (not shown), which is used to produce images of the distal assembly's local environment, in order to facilitate the guiding and positioning of the device inside a patient. The ultrasound probe is particularly useful for procedures involving the ablation of a pancreatic cyst or tumour, as it enables the user to determine the best location in the lower stomach or duodenum for making an incision to access the pancreatic cyst/tumour.

It is also preferable that the device can be operated alongside other instruments to enable practitioners to receive information from the target site. For example, an endoscope may aid the steering of the instruments around obstacles and to a desired position. Other instruments may include a thermometer or camera.

Figure 2:
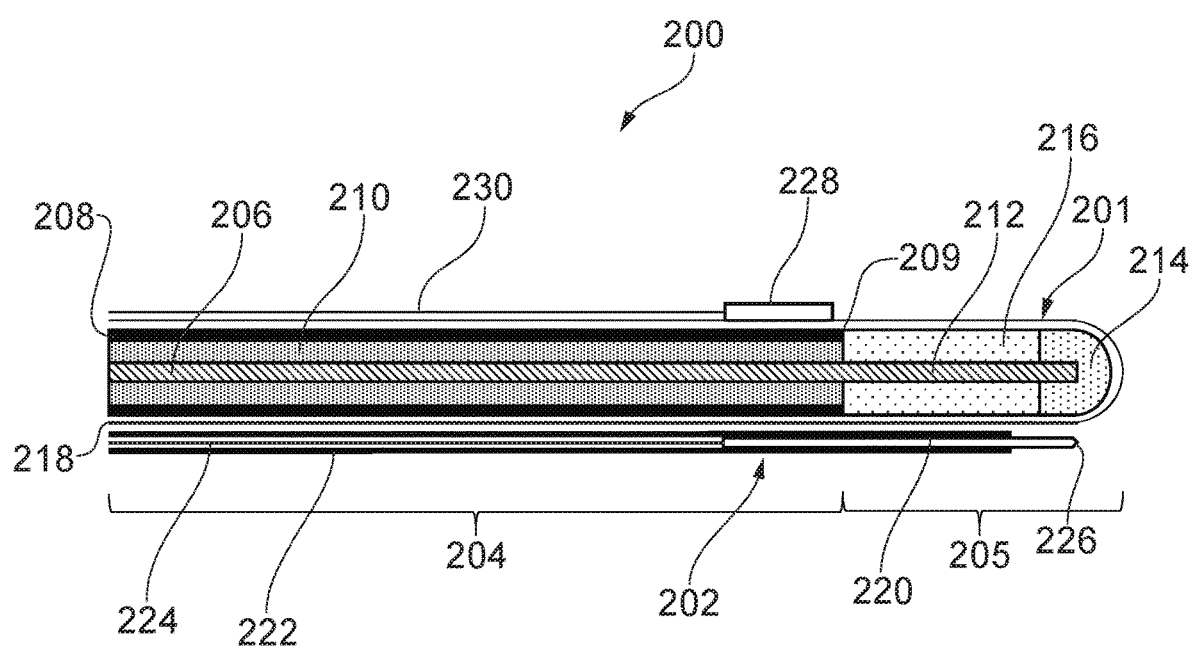
FIG. 2 is a schematic cross-sectional view of a distal end of an ablation instrument suitable for use in the invention.

FIG. 2 is a schematic cross-sectional view of a distal end of a growth ablation device 200 that is an embodiment of the invention. The growth ablation device 200 includes an electrosurgical instrument 201 and a fluid delivery system 202.

Electrosurgical instrument 201 includes a coaxial feed cable 204 that is connected at its proximal end to a generator (such as generator 102) in order to convey microwave energy. The coaxial feed cable 204 comprises an inner conductor 206, which is separated from an outer conductor 208 by a first dielectric material 210. The coaxial feed cable 204 is preferably low loss for microwave energy. A choke (not shown) may be provided on the coaxial cable to inhibit back propagation of microwave energy reflected from the distal end and therefore limit backward heating along the device.

The coaxial feed cable 204 terminates at its distal end with a radiating tip section 205 for radiating microwave energy. In this embodiment, the radiating tip section 205 comprises a distal conductive section 212 of the inner conductor 206 that extends before a distal end 209 of the outer conductor 208. The distal conductive section 212 is surrounded at its distal end by a dielectric tip 214 formed from a second dielectric material, which is different from the first dielectric material 210. The length of the dielectric tip 214 is shorter than the length of the distal conductive section 212. An intermediate dielectric sleeve 216 surrounds the distal conductive section 212 between the distal end of the coaxial cable 202 and the proximal end of the dielectric tip 214. The intermediate dielectric sleeve 216 is formed from a third dielectric material, which is different from the second dielectric material but which may be the same as the first dielectric material 210. The dielectric tip 214 may have any suitable distal shape. In FIG. 2 it has a dome shape, but this is not necessarily essential. For example, it may be cylindrical, conical, etc. However, a smooth dome shape may be preferred because it increases the mobility of the antenna as it is manoeuvred through small channels. The electrosurgical instrument 201 is housed in a protective sheath 218 which electrically insulates the electrosurgical instrument 201. The protective sheath 218 may be made of, or coated with, a non-stick material such as PTFE to prevent tissue from sticking to the instrument.

The properties of the intermediate dielectric sleeve 216 are preferably chosen (e.g. through simulation or the like) so that the radiating tip section 205 forms a quarter wave impedance transformer for matching the input impedance of the generator into a substance (e.g. injected substance) and/or biological tissue load in contact with the radiating tip section 205. This configuration of the radiating tip section 205 may produce an approximately spherical radiation pattern about the radiating tip section 205. This enables the user to accurately radiate target tissue and reduces radiation of or damage to healthy tissue. Depending on the radiation pattern required, different radiating tip section configurations may be used. For example, an asymmetric radiation pattern can be produced by extending the outer conductor 208 along one side of the radiating tip section 205.

The fluid delivery mechanism 202 includes a hollow needle 220 and a fluid conduit 222. An end of the hollow needle 220 is disposed within the fluid conduit 222 such that the two are fluidly connected. The hollow needle 220 is movable within the fluid conduit 222 along its length. The fit between the outer wall of the hollow needle 220 and the inner wall of the fluid conduit 222 may be sufficiently tight such that there are no leakages when the hollow needle 220 is moved. The hollow needle is moved using a control wire 224 which passes through the fluid conduit 222 and is attached to one end of the hollow needle 220. The needle may be fully or partially retracted into the fluid conduit 222, so that its sharp tip 226 does not protrude beyond the distal end of the growth ablation device 200. The fluid conduit 222 may include a valve (not shown) which prevents fluid from leaking out of, or into, the fluid conduit 222 when the hollow needle is in its retracted position. When the user wishes to use the hollow needle (e.g. for piercing tissue or injecting/aspirating fluid), the hollow needle 220 can be exposed such that it protrudes beyond the end of the growth ablation device 200. The fluid delivery mechanism 202 may be fixed relative to the electrosurgical instrument 201, so that the two components form a single integrated device which is configured to fit in the working channel of an endoscope. For example the fluid conduit 222 may be secured to the protective sheath 218 of the electrosurgical instrument 201.

Alternative ways of connecting the hollow needle 220 to the fluid conduit 222 and moving the hollow needle 220 relative to the distal end of the growth ablation device 200 are also possible. For example, the hollow needle 220 may be fixedly connected to the fluid conduit 222. The fluid conduit 222 may then be disposed inside a sleeve through which the fluid conduit 222 and hollow needle 220 may be slid back and forth using a control wire.

The growth ablation device 200 in FIG. 2 also includes an ultrasound probe 228 located near its distal end. The ultrasound probe 228 can be connected to a power supply and monitor (not shown) using wiring 230. The ultrasound probe 230 can be used to produce images of the environment in the vicinity of the distal end of the growth ablation device 200. This enables the distal end of the growth ablation device 200 to be accurately guided to a target location. Other components may also be included near the distal end of the growth ablation device 200. The growth ablation device 200 may include a temperature sensor to monitor the local temperature when microwave energy is applied. The growth ablation device 200 may also include a retractable blade near its distal end for performing incisions. For example, the retractable blade can be exposed in order to make an incision in the lower stomach or duodenal wall in order to access the pancreas. When the blade is not in use, the blade may be retracted so that its sharp edge is not exposed, in order to avoid accidental injuries when the growth ablation device 200 is being guided into position.

In some embodiments, the growth ablation device 200 may also include an outer sheath in which the components at the distal end of the device are housed. The outer sheath may have one or more apertures through which the hollow needle 220 and/or retractable blade may protrude. The outer sheath may have a smooth shape so that no sharp corners are presented to biological tissue, in order to avoid accidental injuries.

Figure 3:
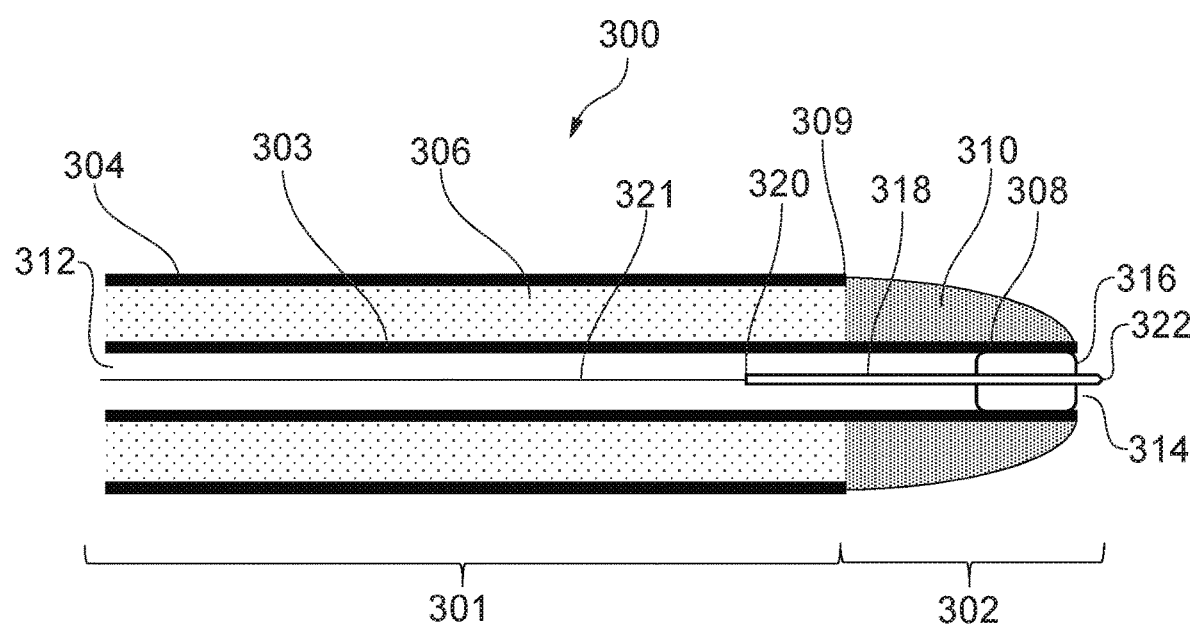
FIG. 3 is a schematic cross-sectional view of a distal end of another ablation instrument suitable for use in the invention.

FIG. 3 is a schematic cross-sectional view of a distal end of a growth ablation device 300 that is another embodiment of the invention. In this embodiment, the fluid delivery system forms part of the electrosurgical instrument. The growth ablation device 300 includes a coaxial feed cable 301, which can be connected at its proximal end to a generator (e.g. generator 102) in order to convey microwave energy. The coaxial feed cable 301 comprises an inner conductor 303, which is separated from an outer conductor 304 by a first dielectric material 306. The coaxial feed cable 301 is preferably low loss for microwave energy. A choke (not shown) may be provided on the coaxial cable to inhibit back propagation of microwave energy reflected from the distal end and therefore limit backward heating along the device.

The coaxial feed cable 301 terminates at its distal end with a radiating tip section 302 for radiating microwave energy. In this embodiment, the radiating tip section 302 comprises a distal conductive section 308 of the inner conductor 303 that extends before a distal end 309 of the outer conductor 304. The inner conductor 303 is hollow, with an inner surface of the inner conductor defining a channel 312 running through the inner conductor 303. The distal conductive section 308 is surrounded at its distal end by a dielectric tip 310 formed from a second dielectric material, which is different from the first dielectric material 306. The dielectric tip 310 is dome-shaped and has a channel running through it, and through which the inner conductor 303 passes. An aperture 314 is formed at the distal end of the inner channel 303.

The channel 312 in the inner conductor 303 can be connected at a proximal end to a fluid delivery device (e.g. a syringe or container) so that the channel 312 may act as a fluid conduit of a fluid delivery system. A hollow needle 318 is located inside the channel 312. The hollow needle 318 has a first end 320 to which a guide wire 321 is attached, and a second end having a sharp tip 322 for piercing biological tissue. The guide wire 321 is used to move the hollow needle 318 back and forth along the length of the channel 312. A plug 316 is located in the aperture 314 of the channel 312. The plug 316 is resiliently deformable to enable formation of a fluid tight seal with the inner surface of the inner conductor 303. Plug 314 has an aperture running through it, through which the hollow needle 318 can be passed. Using the guide wire 321, the hollow needle 318 can be passed through plug 316, so that the sharp tip 322 of the hollow needle 318 protrudes from the plug 316. The hollow needle 318 is then in an exposed position. In this position, when a liquid is fed to the first end 320 of the hollow needle 318, via the channel 312, it can exit through the tip 322 of the hollow needle to the surrounding area, for treatment or otherwise. Similarly, liquid may be aspirated through the hollow needle 318 into the channel 312.

By pulling the guide wire 321, the hollow needle 318 can be retracted such that its tip 322 is situated inside the channel 312 and so no longer exposed to the surrounding area. This is the retracted position. When the hollow needle 318 is in this position, the resiliently deformable nature of the plug 316 ensures that it seals itself, preventing liquid inside the channel 312 from escaping to the surroundings, and preventing liquid or other matter from the surroundings from entering channel 312 and contaminating its contents. The plug 316 may include a one-way valve that permits passage of the needle.

Similarly to the growth ablation device shown in FIG. 2, growth ablation device 300 may include other components such as an ultrasound probe, a temperature sensor or a retractable blade. Growth ablation device 300 may also include a protective outer sheath, for example made of a biologically inert material. Other growth ablation device configurations, other than those shown in FIGS. 2 and 3 are possible.

Figure 4:
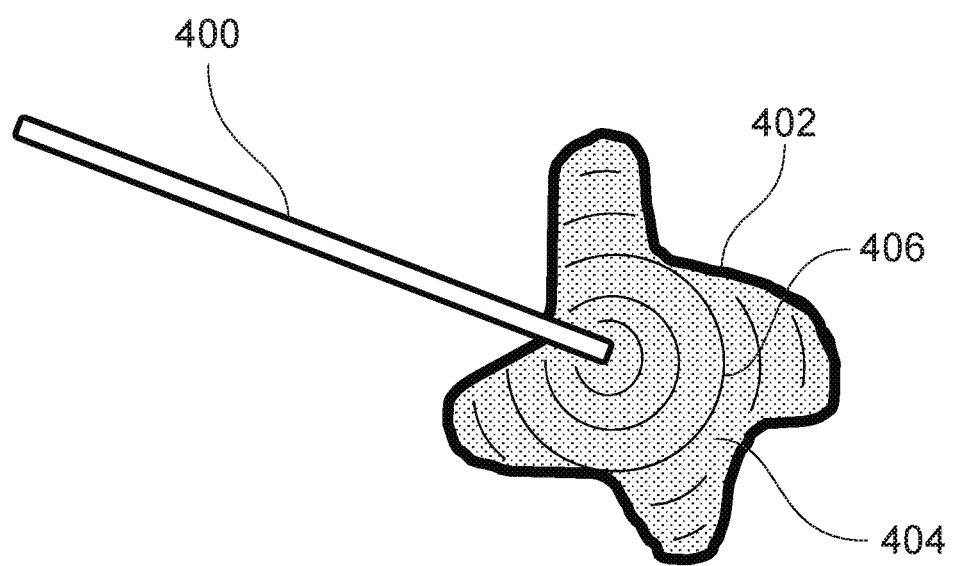
FIG. 4 is a schematic illustration of a tissue ablation method that is an embodiment of the invention.

FIG. 4 shows a schematic illustration of growth tissue ablation using a growth ablation device according to the invention. A growth ablation device 400, such as the devices depicted in FIGS. 2 and 3 is inserted into a void in a growth 402. Using the fluid delivery system of the growth ablation device 400, any fluid in the void 402 is aspirated, e.g. by connecting a proximal end of the fluid conduit to an suitable aspiration or fluid extraction apparatus.

Where the growth ablation device 200 shown in FIG. 2 is used, hollow needle 220 is moved forward using the guide wire 224 so that it is in an exposed position. The hollow needle 220 is used to pierce through the wall of the void 402. The fluid is then aspirated through the fluid conduit 222 via the hollow needle 220, and collected in a collection container (not shown) connected at the proximal end of the fluid conduit 222. A similar procedure may be carried out with growth ablation device 300.

Once the fluid in the void 402 has been aspirated, the fluid delivery system is then used to inject a substance into the void. The volume of substance injected into the void 402 may be the same as the volume of fluid aspirated. This is achieved, for example, by measuring the volume of fluid in the collection container and setting the injection volume accordingly. The injection is performed with the hollow needle 220 still in the exposed position, by causing the substance to flow from a substance container connected to the proximal end of the fluid conduit 222 into the void 402 via the fluid conduit 222 and hollow needle 220. The connections between the containers and fluid conduit are discussed below in relation to FIG. 5.

FIG. 4 shows the void 402 once a substance 404 has been injected into the void. The substance 404 is depicted as the shaded area. After injection of the substance 404, the electrosurgical instrument is used to apply microwave energy to the substance. To do this the radiating tip portion (i.e. the microwave antenna) of the electrosurgical instrument is placed as near as possible to the substance 404. Preferably the radiating tip portion is inserted directly into the void 402 such that it is in contact with the injected substance. Microwave energy is then transmitted to the radiating tip portion via the coaxial feed cable, such that microwave energy radiates from the tip into the substance.

The substance facilitates delivery of treatment energy to biological tissue at the inner surface of the void or growth. This can be done in any of three ways. In one example, the substance presents a thermally conductive medium that assists in the transformation of microwave energy into thermal energy and the communication or transmission of that thermal energy to the biological tissue. In another example, the substance acts as an extension to the radiating tip, so that the microwave energy is radiated at the interface between the substance and the biological tissue. In a third example, the substance acts as a dielectric load for the radiating tip. The properties of the substance may be selected to ensure efficient transfer of the microwave energy from the radiating tip to the biological tissue.

The treatment energy applied to the walls of the void 402 can cause ablation of biological tissue. The transmission of energy is illustrated by radiating lines 406 in FIG. 4.

The void 402 in FIG. 4 is non-symmetrical and has a highly irregular shape. In the absence of any substance injected into the void 402, some portions of the void walls could receive a lower intensity of radiation compared to other portions as they are further away from the radiating tip portion of the electrosurgical instrument. This could lead to uneven ablation of growth tissue around the void, or even some parts of the growth being left substantially unaffected. The substance 404 serves to distribute the energy radiated by the growth ablation device 400 more evenly across the walls of the void 402, so as to provide effective ablation of growth tissue around the entire void 402.

As discussed above, the manner in which the substance transmits energy to the growth tissue depends on the substance used. In some cases, the substance may be a dielectric fluid (e.g. liquid paraffin, acetophenone) which serves to dielectrically load the antenna when the antenna is inserted into the substance. This can improve the efficiency of power delivery to the growth tissue.

In other cases, the substance can form part of the microwave antenna tip, in order to produce a non-symmetrical radiation profile in order to match the shape of the void.

In yet further cases, the substance may have a high dielectric loss factor at the microwave energy frequency used, whereby the substance will heat up with microwave energy is applied to it. Any generated heat in the substance will be distributed throughout the substance via heat conduction processes. Where the substance is in contact with the walls of the void, thermal energy will be transmitted from the substance to the tissue in the wall. This causes heat to be applied evenly across the walls of the void. De-ionised water and/or saline can be used for this purpose. In contrast, if the substance has a low dielectric loss factor at the microwave energy frequency, it may act as a means from transmitting microwave from the antenna to the walls of the void.

In some cases the substance may include materials which are liquid when they are injected, but which will harden or solidify when microwave energy is applied to them. The hardening may occur due to an increase in temperature caused by the microwave energy. Preferably such a substance will have a low dielectric loss factor at the microwave energy frequency. Example substances having such properties are Kolliphor® P 188 and Kolliphor® P 407.

It should be noted that the growth ablation device of the present invention may be used in a mode where no substance is injected into the void. For example, fluid may be aspirated from the void, and the microwave antenna may be inserted into the void (without having injected any substance) to apply microwave energy directly to the void walls. The growth ablation device may also be used to ablate solid growths (i.e. growths which do not have a void), by inserting the microwave antenna directly into the solid growth and applying microwave energy. The growth ablation device of the invention is therefore highly flexible, as it can be used in a variety of different modes, and to ablate different types of growth, depending on the requirements of a particular procedure.

Figure 5:
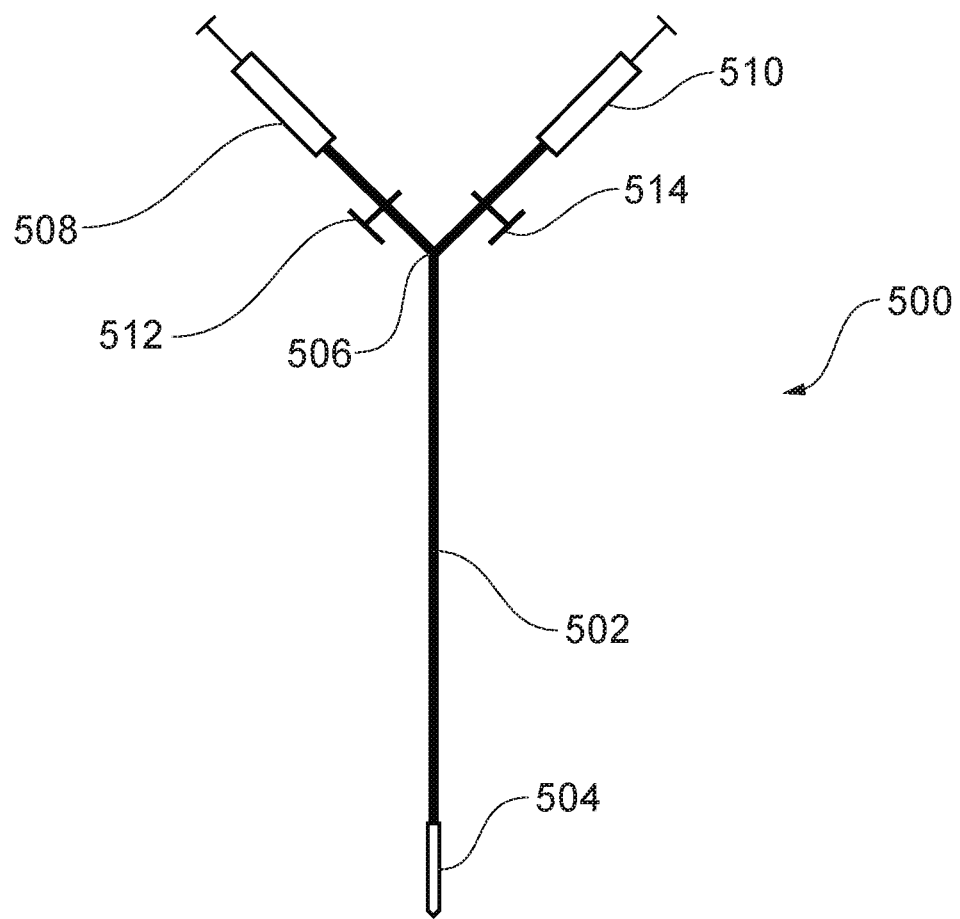
FIG. 5 is a schematic diagram of a fluid delivery mechanism which may form part of an electrosurgical apparatus according to the invention.

FIG. 5 is a schematic diagram of a fluid delivery system 500 which can be used as part of a growth ablation device according to the invention. The fluid delivery mechanism 500 may be integrated with an electrosurgical instrument, for example as discussed in relation to FIG. 2 or 3, in order to form a growth ablation device. The fluid delivery system 500 includes a fluid conduit 502. At its distal end, the fluid conduit 502 is fluidly connected to a hollow needle 504. At its proximal end, the fluid conduit 502 is connected to a T-junction 506. A collection syringe 508 is connected to a first end of the T-junction, and a substance syringe 510 is connected to a second end of the T-junction. The collection syringe 508 can be connected to the fluid conduit 502 by opening valve 512 which is located between the first end of the T-junction 506 and the fluid conduit 502. The substance syringe 510 can be connected to the fluid conduit by opening valve 514 which is located between the second end of the T-junction 506 and the fluid conduit 502.

Thus, when fluid is to be aspirated from a void in a growth, valve 514 is closed and valve 512 is opened, such that the collection syringe 508 is fluidly connected to the hollow needle 504 via the fluid conduit 502. Fluid located near the tip of the hollow needle 504 can be aspirated into the collection syringe 508 using the piston of the syringe. When a substance is to be injected, valve 512 is closed and valve 514 is opened, such that substance syringe 510 is fluidly connected to the hollow needle 504 via the fluid conduit 502. A volume of substance can then be injected from the substance syringe 510 into a target area via the hollow needle 504. The valves and syringes may be controlled manually or automatically (e.g. using a controller), so that use of the fluid delivery mechanism 502 may be substantially automated.

In alternative configurations, the fluid conduit 502 may not be connected to a T-junction. In this case, the syringes can be connected directly to the proximal end of the fluid conduit, and must be exchanged depending on the operation to be carried out (i.e. fluid aspiration or substance injection). Other suitable fluid delivery mechanisms other than syringes may be used. For example, a container coupled to a pump could be used for collecting and/or injecting fluid.

The invention claimed is:

1. An electrosurgical apparatus for treating a biological growth that contains a fluid-filled sac, the apparatus comprising:
an electrosurgical instrument for delivering microwave energy into biological tissue, the electrosurgical instrument comprising:
a coaxial cable for conveying microwave energy; and
a radiating tip portion disposed at a distal end of the coaxial cable to receive microwave energy from the coaxial cable; and
a fluid delivery mechanism for transporting fluid to and from a treatment zone located around the radiating tip portion,
wherein the fluid delivery mechanism comprises:
a flexible fluid conveying conduit that extends along the coaxial cable, and
a rigid insertion element in fluid communication with a distal end of the fluid conveying conduit and arranged to extend into the treatment zone, wherein the rigid insertion element comprises a hollow needle,
wherein the fluid delivery mechanism is arranged:
to aspirate fluid from the treatment zone, and
to inject a substance into the treatment zone to replace the aspirated fluid, and
wherein the substance has dielectric properties selected to facilitate uniform delivery of treatment energy to biological tissue in the treatment zone.

2. An electrosurgical apparatus according to claim 1, wherein the treatment zone includes a fluid-filled sac contained within a biological growth, whereby the fluid delivery mechanism is arranged to replace biological fluid in the fluid-filled sac with the substance.

3. An electrosurgical apparatus according to claim 1, wherein the fluid delivery mechanism is arranged to inject a volume of the substance into the treatment zone that is equal to a volume of the fluid aspirated from the treatment zone.

4. An electrosurgical apparatus according to claim 1, wherein the substance consists of a dielectric fluid.

5. An electrosurgical apparatus according to claim 1, wherein the substance comprises de-ionised water or saline.

6. An electrosurgical apparatus according to claim 1, wherein the substance extends the radiating tip portion.

7. An electrosurgical apparatus according to claim 1, wherein the substance is selected to transition from a liquid phase to a solid phase during application of microwave energy to the treatment zone.

8. An electrosurgical apparatus according to claim 1, wherein the coaxial cable comprises an inner conductor, an outer conductor, and a first dielectric material separating the inner conductor and outer conductor, and wherein the inner conductor is hollow to provide a passageway for the fluid delivery mechanism.

9. An electrosurgical apparatus according to claim 8, wherein the rigid insertion element is in fluid communication with the flexible fluid conveying conduit via the passageway.

10. An electrosurgical apparatus according to claim 8, wherein the rigid insertion element is slidably mounted in the passageway.

11. An electrosurgical apparatus according to claim 1, wherein the rigid insertion element is movable between an exposed position where it protrudes beyond the distal end of the electrosurgical instrument, and a retracted position in which it is set back from the distal end of the electrosurgical instrument.

12. An electrosurgical apparatus according to claim 1, wherein the electrosurgical instrument comprises an ultrasound probe for producing images of a patient's internal organs.

13. An electrosurgical apparatus according to claim 1 further comprising:
a generator for generating the microwave energy; and
a surgical scoping device for non-percutaneous insertion into a patient's digestive tract, the surgical scoping device having an instrument channel running along its length,
wherein the electrosurgical instrument and fluid delivery mechanism are conveyed within the instrument channel of the surgical scoping device, and
wherein the coaxial cable is connected to receive the microwave energy from the generator.

14. A method for treating a biological growth that contains a fluid-filled sac, the method comprises:
non-percutaneously inserting an instrument cord of a surgical scoping device into a patient's digestive tract, the surgical scoping device having an instrument channel running along its length;
conveying an electrosurgical instrument and a fluid delivery mechanism along the instrument channel of the surgical scoping device,
wherein the electrosurgical instrument comprises a coaxial cable for conveying microwave energy, and a radiating tip portion disposed at a distal end of the coaxial cable to receive microwave energy from the coaxial cable, and wherein the fluid delivery mechanism comprises a flexible fluid conveying conduit that extends along the coaxial cable, and a rigid insertion element in fluid communication with a distal end of the fluid conveying conduit, wherein the rigid insertion element comprises a hollow needle;

inserting the hollow needle of the rigid insertion element into a fluid-filled sac contained within a biological growth located at the distal end of the instrument cord;

aspirating fluid from the fluid-filled sac;

injecting a substance into the fluid-filled sac to replace the aspirated fluid; and delivering microwave energy to the radiating tip portion, wherein the substance has dielectric properties selected to facilitate uniform delivery of treatment energy to biological tissue surrounding the fluid-filled sac.

15. An electrosurgical apparatus for treating a biological growth that contains a fluid-filled sac, the apparatus comprising:

an electrosurgical instrument for delivering microwave energy into biological tissue, the electrosurgical instrument comprising:

a coaxial cable for conveying microwave energy; and a radiating tip portion disposed at a distal end of the coaxial cable to receive microwave energy from the coaxial cable; and a fluid delivery mechanism for transporting fluid to and from a treatment zone located around the radiating tip portion, wherein the fluid delivery mechanism comprises:

a flexible fluid conveying conduit that extends along the coaxial cable, and a rigid insertion element in fluid communication with a distal end of the fluid conveying conduit and arranged to extend into the treatment zone, wherein the fluid delivery mechanism is arranged:
to aspirate fluid from the treatment zone, and
to inject a substance into the treatment zone to replace the aspirated fluid, and wherein the substance has dielectric properties selected to facilitate uniform delivery of treatment energy to biological tissue in the treatment zone; and wherein the substance is selected to transition from a liquid phase to a solid phase during application of microwave energy to the treatment zone.

16. A method for treating a biological growth that contains a fluid-filled sac, the method comprises:

non-percutaneously inserting an instrument cord of a surgical scoping device into a patient's digestive tract, the surgical scoping device having an instrument channel running along its length;

conveying an electrosurgical instrument and a fluid delivery mechanism along the instrument channel of the surgical scoping device, wherein the electrosurgical instrument comprises a coaxial cable for conveying microwave energy, and a radiating tip portion disposed at a distal end of the coaxial cable to receive microwave energy from the coaxial cable, and wherein the fluid delivery mechanism comprises a flexible fluid conveying conduit that extends along the coaxial cable, and a rigid insertion element in fluid communication with a distal end of the fluid conveying conduit;

extending the rigid insertion element into a fluid-filled sac contained within a biological growth located at the distal end of the instrument cord;

aspirating fluid from the fluid-filled sac;

injecting a substance into the fluid-filled sac to replace the aspirated fluid; and delivering microwave energy to the radiating tip portion, wherein the substance has dielectric properties selected to facilitate uniform delivery of treatment energy to biological tissue surrounding the fluid-filled sac, and wherein the substance is selected to transition from a liquid phase to a solid phase during application of microwave energy to a treatment zone.

* * * * *